(12) United States Patent
Bevilacqua et al.

(10) Patent No.: US 11,048,466 B2
(45) Date of Patent: Jun. 29, 2021

(54) COGNITIVE IMPROVEMENT SYSTEM AND METHOD OF TESTING

(71) Applicant: Andy Bevilacqua, Huntsville, AL (US)

(72) Inventors: Andy Bevilacqua, Huntsville, AL (US); Roy Brown, Huntsville, AL (US); Casey Catron, Huntsville, AL (US)

( * ) Notice: Subject to any disclaimer, the term of this patent is extended or adjusted under 35 U.S.C. 154(b) by 0 days.

(21) Appl. No.: 16/735,544

(22) Filed: Jan. 6, 2020

(65) Prior Publication Data

US 2020/0142659 A1 May 7, 2020

Related U.S. Application Data

(63) Continuation-in-part of application No. 16/281,095, filed on Feb. 21, 2019, now Pat. No. 10,564,422, which is a continuation-in-part of application No. 15/409,518, filed on Jan. 18, 2017, now Pat. No. 10,482,779, which is a continuation-in-part of application No. 15/095,824, filed on Apr. 11, 2016, now Pat. No. 10,242,584.

(60) Provisional application No. 62/929,592, filed on Nov. 1, 2019, provisional application No. 62/146,050, filed on Apr. 10, 2015.

(51) Int. Cl.
*G06F 3/147* (2006.01)
*A61B 3/10* (2006.01)

(52) U.S. Cl.
CPC .............. *G06F 3/147* (2013.01); *A61B 3/10* (2013.01)

(58) Field of Classification Search
CPC ............ G06F 3/147; G09G 3/002; A61B 3/10
See application file for complete search history.

(56) References Cited

U.S. PATENT DOCUMENTS

| 8,328,354 B2 * | 12/2012 | Li | A61B 3/08 351/201 |
|---|---|---|---|
| 2013/0114850 A1 * | 5/2013 | Publicover | H04N 5/247 382/103 |
| 2013/0115576 A1 * | 5/2013 | Grant | G09B 9/16 434/30 |
| 2013/0222235 A1 * | 8/2013 | Abdollahi | G09G 5/006 345/156 |
| 2016/0178904 A1 * | 6/2016 | Deleeuw | G06F 3/011 345/8 |

* cited by examiner

*Primary Examiner* — James S. McClellan
(74) *Attorney, Agent, or Firm* — Chris Tanner; FYPA PLLC

(57) ABSTRACT

An assortment of Cognitive Load Reduction (CLR) systems is disclosed. The systems are worn by a user, rather than appearing on displays in front of the user. This arrangement allows the systems to be movable and less confining. This in turn results in the wearer employing the CLR systems in a wider variety of environments than earlier mechanisms.

18 Claims, 20 Drawing Sheets

Time vs Gender

Time vs Movement Type

Time vs Contrast of the Movement on the display

Fig. 10

Correlations

|  |  | Meantime | AGE |
|---|---|---|---|
| Meantime | Pearson Correlation | 1 | .338** |
|  | Sig. (2-tailed) |  | .001 |
|  | N | 100 | 100 |
| AGE | Pearson Correlation | .338** | 1 |
|  | Sig. (2-tailed) | .001 |  |
|  | N | 100 | 100 |

**. Correlation is significant at the 0.01 level (2-tailed).

Age is a Strong Covariate for Time vs Task

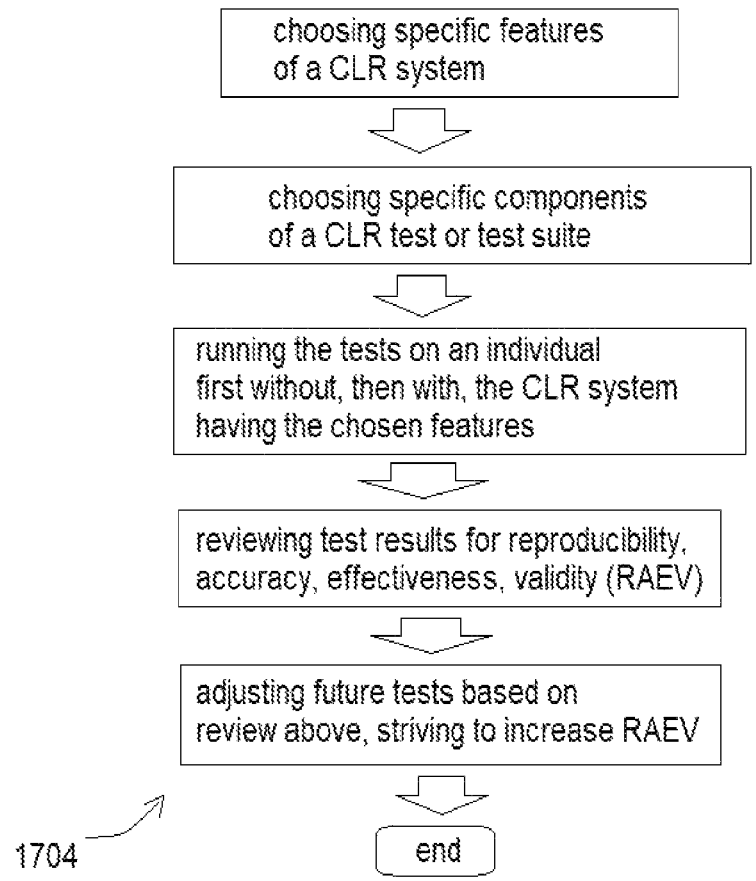
FIG. 17A (testing per individual)

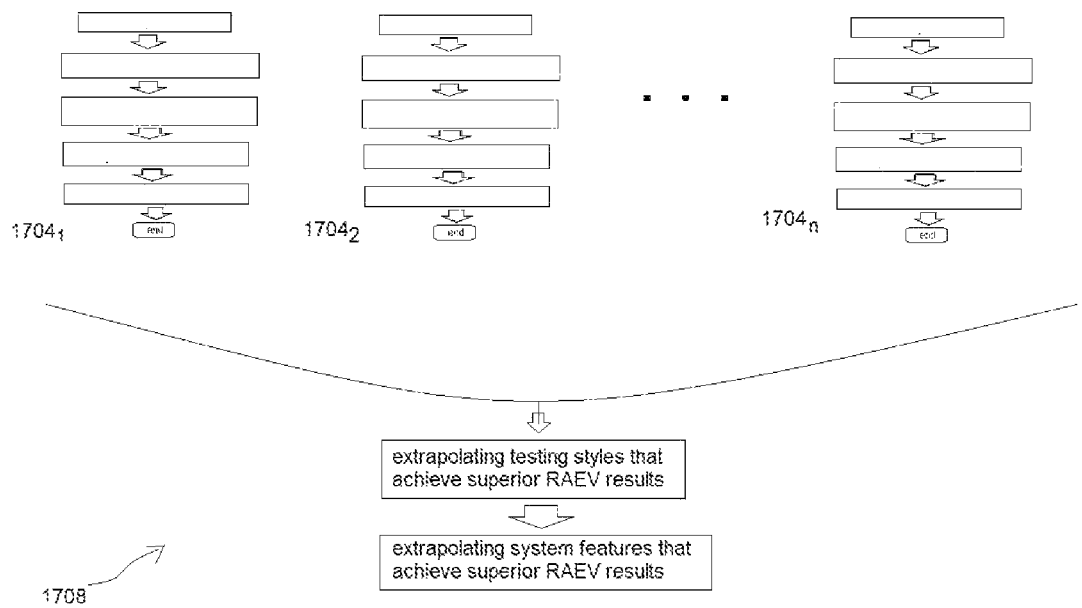
FIG. 17B (testing in aggregate/groups)

COGNITIVE IMPROVEMENT SYSTEM AND METHOD OF TESTING

PRIORITY INFORMATION

This application claims priority to co-pending U.S. patent application Ser. No. 15/409,518 filed Jan. 18, 2017 and entitled "Cognitive Function Improvement System and Method", and claims priority to co-pending U.S. patent application Ser. No. 15/095,824 filed Apr. 11, 2016 and entitled "Cognitive Function Improvement System and Method", which claims priority to co-pending U.S. Provisional Patent Application Ser. No. 62/146,050 filed Apr. 10, 2015 and entitled "Cognitive Function Improvement System and Method," all of which are incorporated herein by reference.

BACKGROUND

Throughout this disclosure, the expressions Cognitive Load, Cognitive Load Reduction, and Cognitive Load Theory will be capitalized, as they are terms of art. Cognitive psychology refers to the total amount of mental effort being used in the working memory. Cognitive Load Theory is a concept that the instructional design by an instructor, teacher, professor or the like can be configured in order to reduce the cognitive load in learners. The concept is based upon the desire to ease the mental effort needed process information including, cognitive tasks, learnings, processing, etc. In theory, a heavy cognitive load will have a negative effect on the completion of other metal task, thus making it harder for that individual to process information.

Research has shown that elderly, school aged students, and children experience cognitive load differently and typically at higher levels. Proper Cognitive Load should assist in the presentation of information in a manner that encourages the viewer or learner of that information to optimize their intellectual performance.

According to Cognitive Load Theory (CLT), human working memory is limited in both its capacity to store information and the duration with which it can be stored. Within working memory, sensory processing, i.e. visual, auditory and tactile information is processed before being passed on to long-term memory in the form of categorical information (such as schemas) for encoding and storage. Cognitive Load Theory holds that as immediate sensory inputs aggregate, they tend to fill up the available processing space within working memory, resulting in a decrease in efficiency within the entire memory system. Conventional research offers that these elements of load can have severe implications with reference to an individual's learning ability, memory retention and general problem solving ability. In CLT, one would expect a peripheral task-irrelevant stimulus to impose an extraneous cognitive load and reduce task performance, under the assumption that the cognitive task is complex.

One area of conventional theory is directed at far field peripheral processing and its effects on the load theory of selective attention and cognitive control. This theory is an extension of perceptual load theory and deals primarily with the visual cognitive load induced by the attentional perceptual processing of visual information. One of the central issues addressed by this research is the problem of distractors within the peripheral field of view, and the effect of perceptual cognitive load on a person's ability to consciously process the presence of a distractor.

A distractor can be classified as any type of movement within the field of view of the eye. It is believed that sensory responses to distractors within the field of view are only noticed when load of the main perceptual task is low, and when the processing of the distractors is relevant for the stimuli to be processed in the main perceptual task. According to the researchers, responses to these distractors are reduced the more the processing load of the main perceptual task increases. These findings appear to be supported by FMRI (Functional Magnetic Resonance Imaging) studies that show motion-related activity is reduced in the cortical V5 region of the brain during high cognitive load tasks.

Another issue concerns the lack of experimentation in the far peripheral field. The common method used in most of the experiments supporting perceptual load theory is to use either a field of dots moving from the center of the field of view (foveal) towards the edge of a computer screen or a distractor just outside of the central field of the eye in the parafoveal or near peripheral field.

Conventional research shows that because the biological functions of foveal (central) and peripheral vision are so different, the processing of the information collected by these areas actually takes place within separate regions of the brain, making far peripheral processing an idiosyncratic process. This could mean that far peripheral field processing is not bound by selective attention in the same way foveal and parafoveal vision seems to be. Under perceptual load theory, one would expect the peripheral stimulus to have no effect if the cognitive task is complex. This leaves open the question regarding whether movement within the far peripheral field (50-90 degrees) will produce measurable cognitive load outside of human selective attention.

Typically, each eye can see in a range of approximately 120 degrees of an arc in a horizontal field. Most of that arc is defined as peripheral vision and the human brain and eye in conjunction do not always process information in the peripheral vision areas in the same manner as information received in the center of vision for that individual. The center vision, which can also be classified as the center of gaze, typically coordinates with the center of the person's face and has a range of about 20 degrees either side of the center of the vision.

In light of the above, what is needed is a new system, apparatus, and method of manipulating (either up or down) the cognitive load on an individual using movement somewhere from the center to the far periphery of vision to effect information processing, task processing, and mental performance of that individual as desired to meet a particular task demand. This needed system, apparatus, and method is lacking in the art.

SUMMARY OF THE EMBODIMENTS

The embodiments herein generally relate to altering the cognitive load in an individual to affect the information and task processing of that individual. This is achieved by introducing movement in different parts of the visual field to affect the cognitive load thereby allowing the user to be more or less efficient at the task or information processing.

Embodiments of headwear for reduce the cognitive load in a user. The headwear embodiments compromise a frame shaped to be positioned on the head of the user, and first and second display screens attached to the frame. A processor is operatively attached to the frame, the first display screen, and the second display screen. The processor is configured to instruct the first display screen and the second display screen to display repetitive, non-biological movement.

BRIEF DESCRIPTION OF THE DRAWINGS

FIG. 10 is a chart showing age as a factor in the correlation of time to complete the task;

FIGS. 17A and 17B shows testing methodologies for individuals and groups, respectively.

DETAILED DESCRIPTION OF PREFERRED EMBODIMENTS

Figure 1:
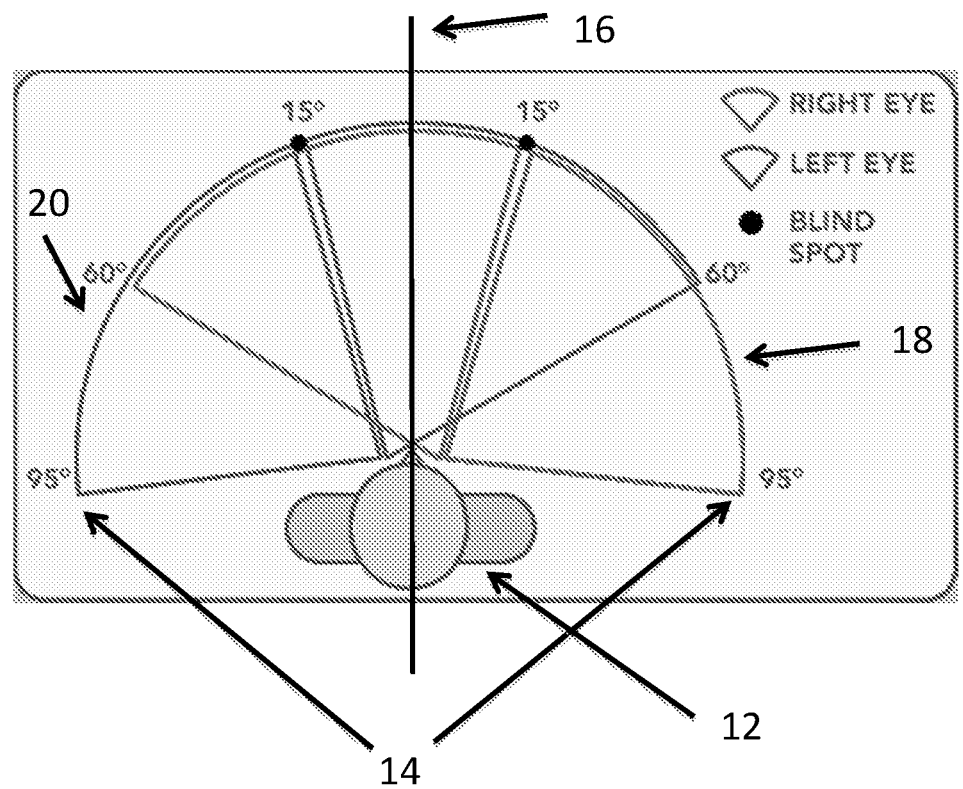
FIG. 1 shows a plan view of the field of vision of an average individual.

FIGS. 1-10 show an example system 10 for reducing Cognitive Load. Within this disclosure, positional terms such as "upper", "lower", "side", "top", "bottom", "vertical", or "horizontal" etc. refer to the apparatus when in the orientation shown in the drawing. The skilled artisan will recognize that objects in accordance with the present disclosure can assume different orientations when in use.

The system 10 reduces a Cognitive Load in a user 12 having a field of vision 14, a center of vision 16, a right eye peripheral vision 18, and a left eye peripheral vision 20.

Figure 2:
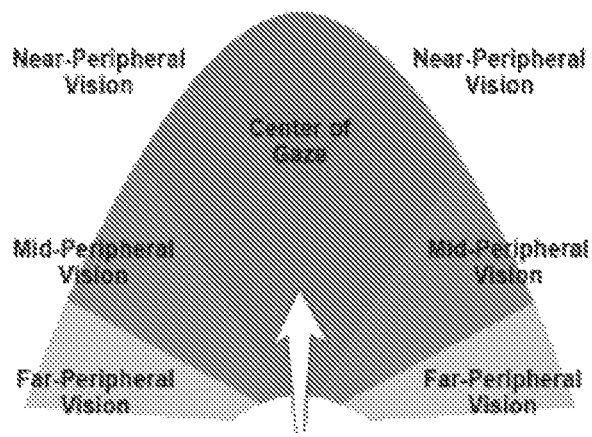
FIG. 2 shows a general breakdown of the peripheral vision portions in the average individual.

As shown in FIG. 2, generally, the right eye peripheral vision 18 and the left eye peripheral vision 20 each include a horizontal field range of vision of approximately 100 degrees as measured from the center of vision 16. Typically, the center of vision 16 starts at a 0 degree point at a position corresponding to the center of the head of the user 12.

Repetitive, non-biological movement can be important in reduction of Cognitive Load. For example, there are four major types of movement: biological movement, non-biological movement, repetitive movement, and directional movement. Conventional research has offered that any movement in the peripheral vision range increases the cognizant load. The current inventor has discovered that of these four types of movement, certain movements actually do increase the cognitive load. Conversely, some of the movements actually reduce the cognitive load, thereby increasing the cognitive brain function on a desired task.

Biological movement as well as directional movements in the peripheral vison areas tend to attract, at least on a subconscious level, the attention of an individual that perceives this movement, thereby taking some brain function away from a preferred task at hand. Conversely, however, non-biological movement, especially in a repetitive manner, tends to facilitate an individual focusing more on the task at hand thereby reducing the cognitive load on that individual and allowing more cognitive learning and processing of the preferred task at hand. This has also proven effective when the repetitive, non-biological movement can block out the other biological and/or directional movement.

As will be discussed in more detail herein, testing has shown that the repetitive movement in numerous directions can counteract the effect of a user's eyes preference for certain directional movement. For example, a wide variety of starbursts, or multiple line movements in various directions has proven to be preferred over a repetitive bouncing motion like in a pong game.

Thus, the motions, while repetitive, need to be multidirectionally repetitive. Additionally, testing shows that a purely directional motion that is repeated was not as effective at significantly reducing the cognitively load as a repetitive multidirectional movement. Further, non-biological movement has been proven to be more effective than the biological movement. This can be due to various instincts in the user, such as survival instincts, that may forcibly take over when a biological movement is perceived in this peripheral vision area, where those instincts are non-blockable.

As shown in FIG. 2, peripheral vision can be broken down into near peripheral vision which is the vision just adjacent to the center of vision, mid-peripheral vision, which is beside the near peripheral vision, and then far peripheral vision which is at the edge of the field of view. With healthy and normal eyes, using a zero degree base point as extending from the center of the head, the healthy eye should be able to see approximately 95 degrees temporally, or towards the ear, and approximately 60 degrees nasally, or towards the nose, as measured from that center zero location. Further, the healthy eye should be able to see 60 degrees above and 75 degrees below the vertical center line of each eye. As such, the horizontal field range is approximately 155 degrees and the vertical field range is approximately 135 degrees at any given time for each eye.

Again, in this range of vision, conventional research tends to show that movement and/or distractions in the peripheral vision areas will increase the cognitive load and thereby reduce the efficiency of the active task, such as learning or information processing. Alternatively, non-biological movement, within the center of vision, where such task is the focus of that individual will either increase or decrease cognitive load depending on the characteristics of movement.

Figure 3:
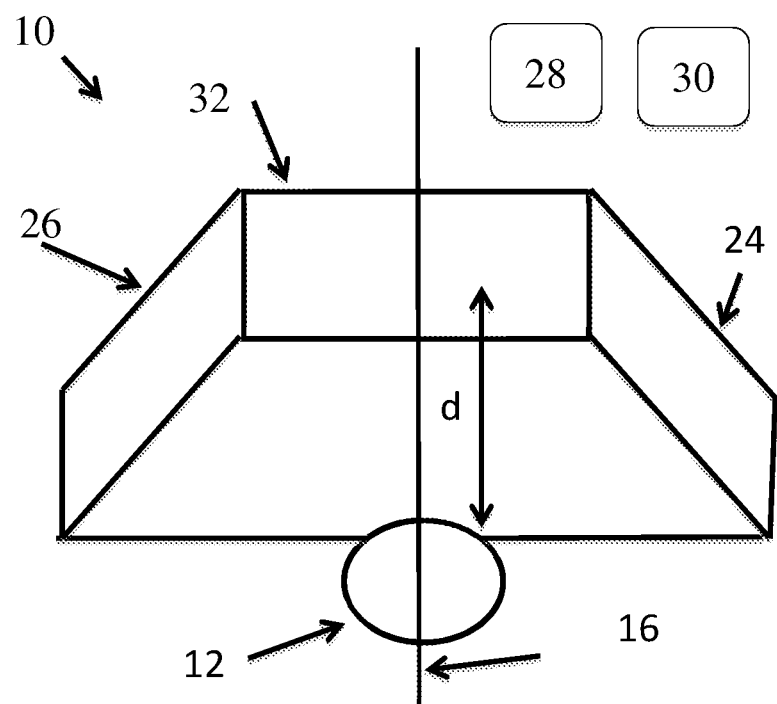
FIG. 3 shows a schematic of a system made in accordance with the embodiments herein.

FIG. 3 demonstrates one potential way that the system 10 instructs the display screens 24 and 26 to display repetitive, non-biological movement. In an embodiment, these instructions can originate in a computer readable memory medium 30 through the processor 28.

Figure 5:
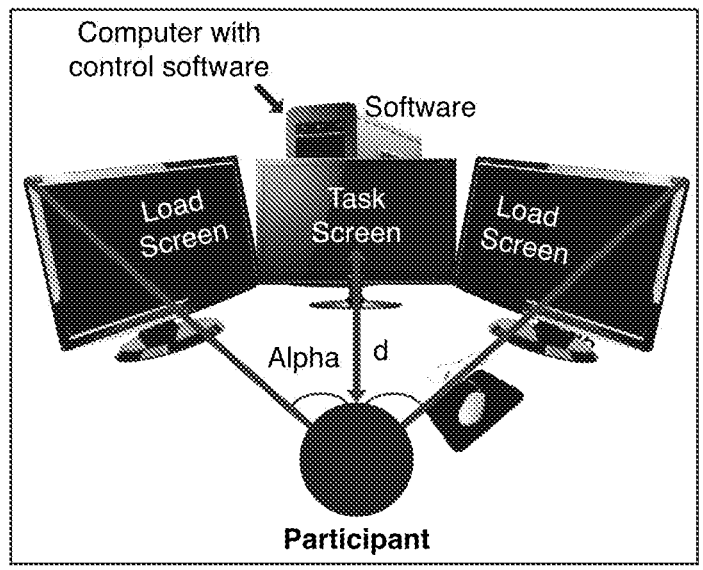
FIG. 5 shows an example test system.
Figure 6:
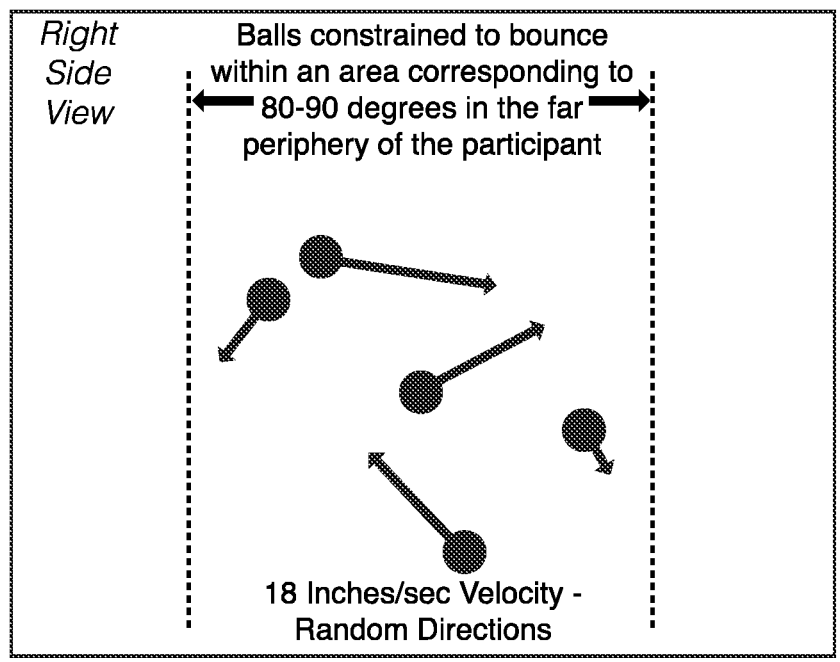
FIG. 6 shows an example of repetitive non-biological movement used in a test system.

One example of a test environment is shown in FIG. 5. However, as will be discussed in more detail herein, many other test environments exist. An example group of tests had ~50 subjects participated and were set up with a system for achieving Cognitive Load Reduction. An experiment used a set of 5 moving balls that could be displayed at locations approximately 80 to 90 degrees from the center of vision 16, as shown at least within FIG. 6.

The participants were required to do a cognitive process/test. The elapsed times to complete those tasks were recorded. The results showed that when the repetitive non-biological movement, in this case the bouncing balls, was in the far peripheral vision of the user, that user completed a cognitive task at a statistically significant faster pace. Further, the data showed that male participants responded with higher reductions in Cognitive Load, when compared to the absence of the repetitive, non-biological movement, than females. As such, the current system could be focused on male cognitive load reduction, but could be proven to be statistically significant for females as well. The bouncing ball paradigm had both vertical and horizontal components to the movement as well as rapid changes in directions, but otherwise eye threshold information was used for the eye to have the ability to see colors, brightness, direction, and velocity changes.

Figure 7:
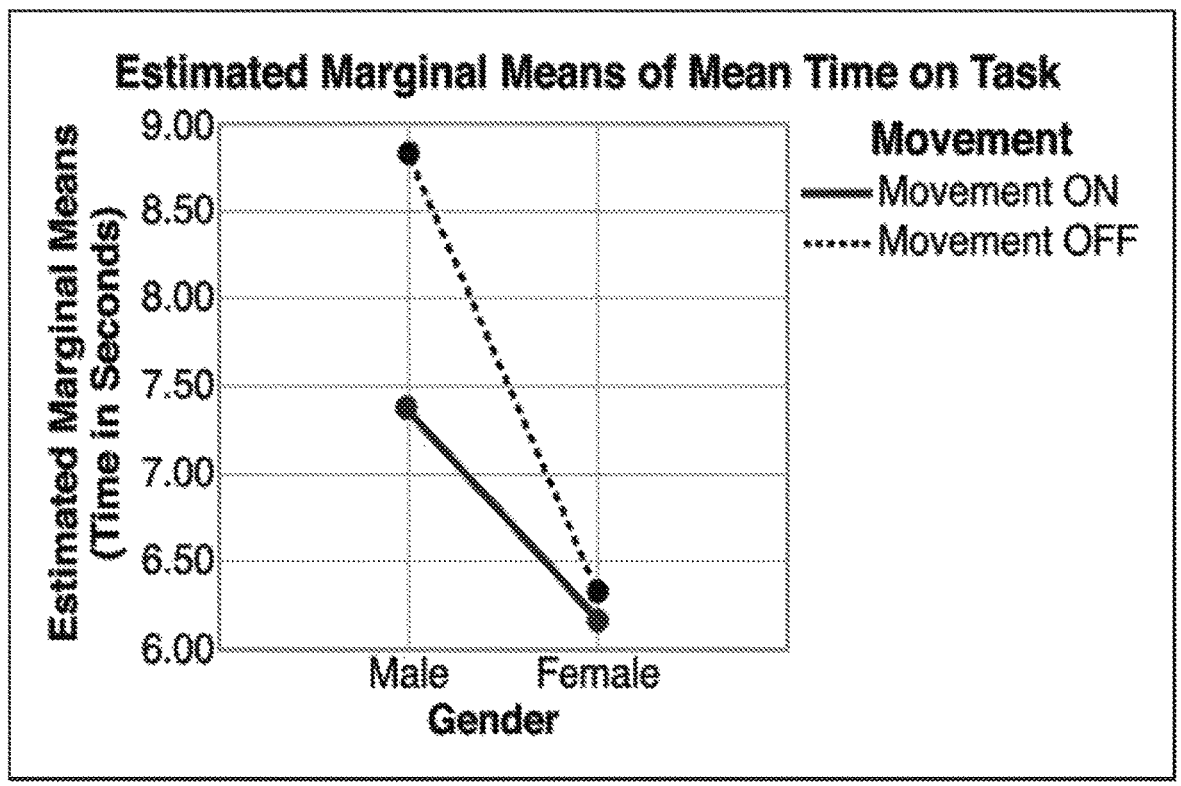
FIG. 7 shows a chart showing the estimated marginal means of mean time to complete a task, including times for each gender both with and without non-biological movement.
Figure 8:
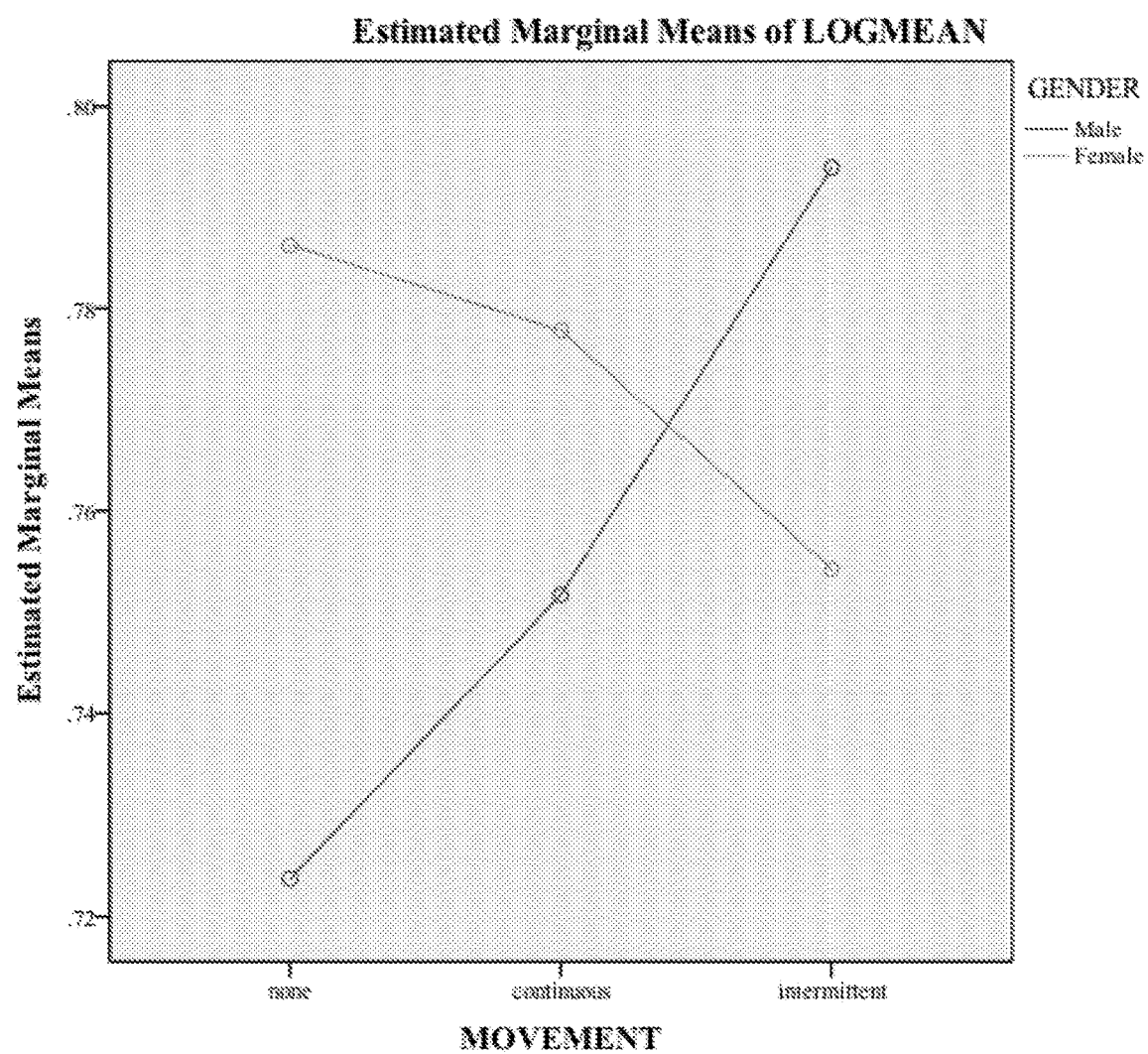
FIG. 8 is a chart showing the estimated marginal means of time to complete a task for each gender, mapped against no movement, continuous movement, and intermittent non-biological movement conditions.

FIGS. 7-10 show empirical results of various experiments with certain variables correlated with the task complete times. FIG. 7 shows the differences in the mean times to complete a task both with and without the repetitive, non-biological movement for each gender. FIG. 8 shows the differences in the mean times to complete a task for each gender when the non-biological movement was varied from off, to continuous, to intermittent. This intermittent time could vary from an on/off laps of 0-20 seconds, 0-10 seconds, or 0-5 seconds, which was tested.

Figure 9:
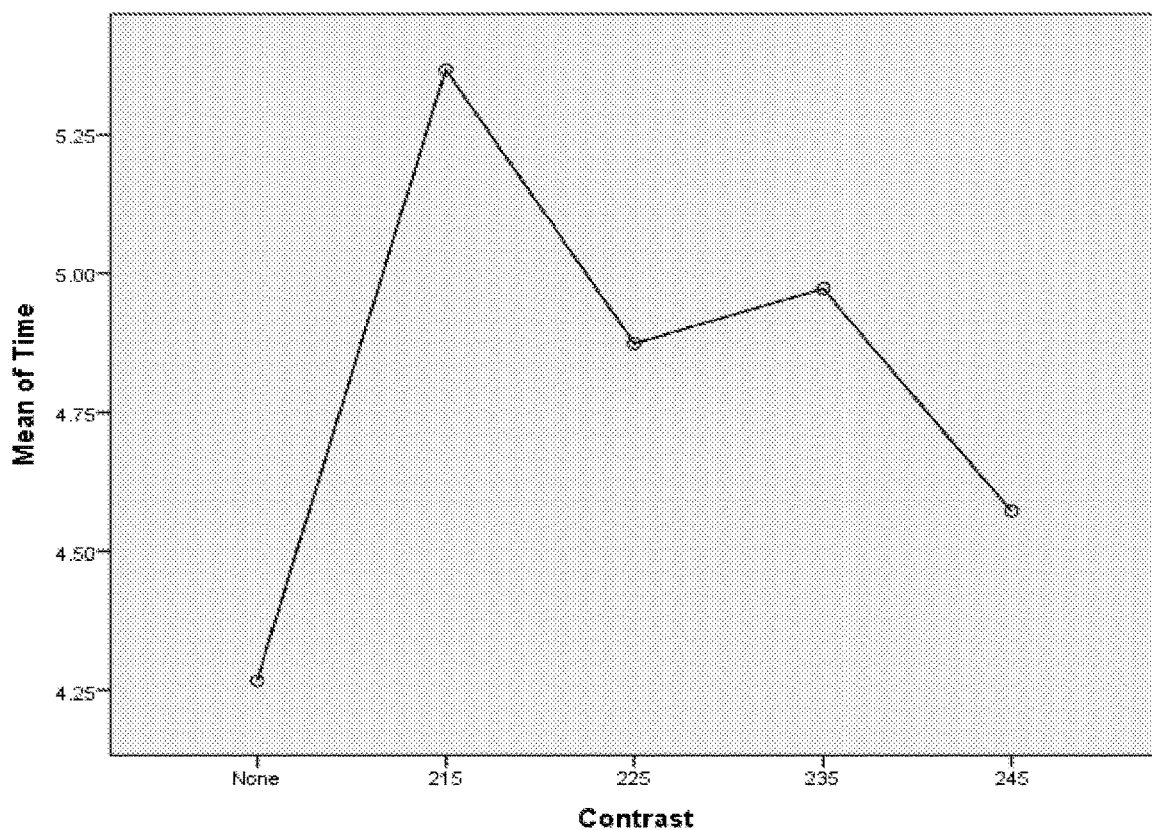
FIG. 9 is a chart showing the mean of time to complete a task mapped against varying levels of contrast of intermittent non-biological movement.

FIG. 9 charts some differences in mean times to complete a task when the contrast of the non-biological movement varied on the display. Finally, FIG. 10 explains that the age of the individual viewing the non-biological movement and the task is a covariate, or predictor of success in the speed of completion of the task.

Even though the results may be varied, the common denominator is that the inventor could actively change cognitive load levels through the use of movement. The use of movement is effective for viewing from the center of vision all the way out to the periphery. The factors of the location of the movement, what is the movement, and the properties of that movement when it is presented changes the results of the central task attempted.

Other variables could impact determining the best display factors for the movement. For example, the direction and speed of the movement can be important, especially if the direction and speed support or refute the non-biological nature of the movement. Other factors include the color, contrast, size, and shape of the object moving. Characteristics of the movement itself can also be a factor in the effectiveness of the change in cognitive function by this method and system. For example, the frequency of the movement of the objects, the quantity of objects moving and the density of the objects on the display can be altered to maximize or minimize cognitive function in the individual. Further, the frequency of the appearance of the object moving can be adjusted in relation to the flicker fusion threshold, or flicker fusion rate, to maximize or minimize cognitive function in the individual. The flicker fusion threshold the frequency at which an intermittent light stimulus appears to be completely steady to the average human observer.

An embodiment includes an object specifically picked by one or more of color, contrast, size, shape and quantity. That object(s) could then selectively be moved in a direction, at a speed, and/or in a frequency to maximize cognitive function in the individual as desired by the administrator of the method and/or system.

As previously mentioned, characteristics of the individual, or observer of the display, can affect the effectiveness of the movement in altering the cognitive load and completion time of the task or comprehension of the information provided. As shown in FIG. 10, the age of the individual as well as gender affected the results. Other factors of the individual him/herself can be used in determining the best object and movement of that object to result in the desired change in cognitive load. These demographic variables can include the afore mentioned gender and age, and could further include some single selection or combination of the emotional status, fatigue, race, ethnicity, education level, current health status, and even the time of day of the observation by the individual. Again, a preferred embodiment of the method and system would be to adjust the movement based upon one or more the demographic variables of the individual to further influence the cognitive abilities of the individual experiencing the movement.

As shown in FIG. 3, the computer readable memory 30 can work in conjunction with other memory media to provide the instructions to the display screens 24, 26, and 32. For example storage media can store the data and instructions that will be used to display on the display screens 24, 26, and 32. Transmission media can be used to link the processor 28, computer readable memory 30, and any storage media. Additionally, a host server can be connected to the processor 28 and/or the computer readable memory 30 through a communications network to provide data and instructions to the system and to support interactivity between the instructor and user of the system.

Figure 4A:
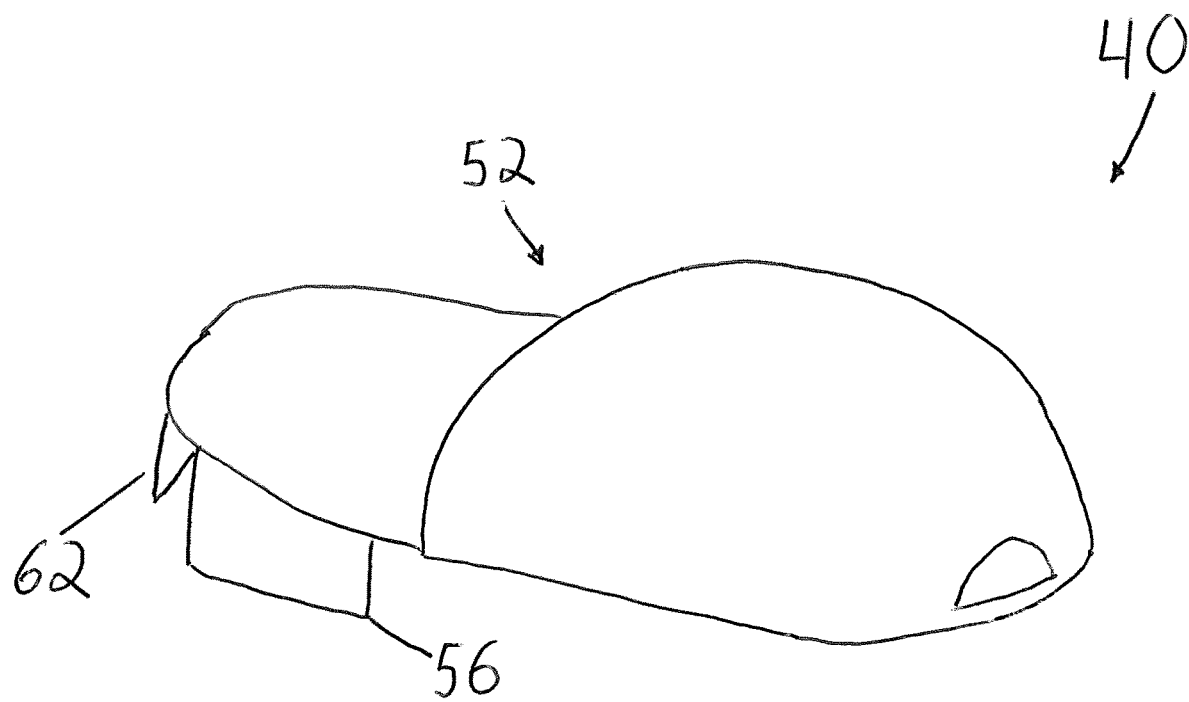
FIG. 4A is a rear perspective view of an example of headwear embodiment.
Figure 4B:
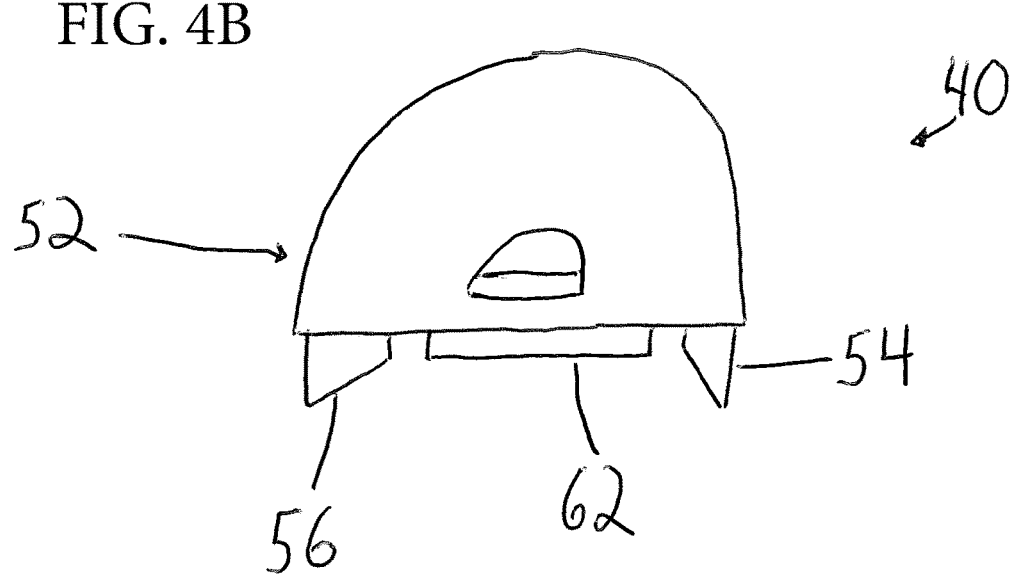
FIG. 4B is a rear view of an example headwear embodiment.
Figure 4C:
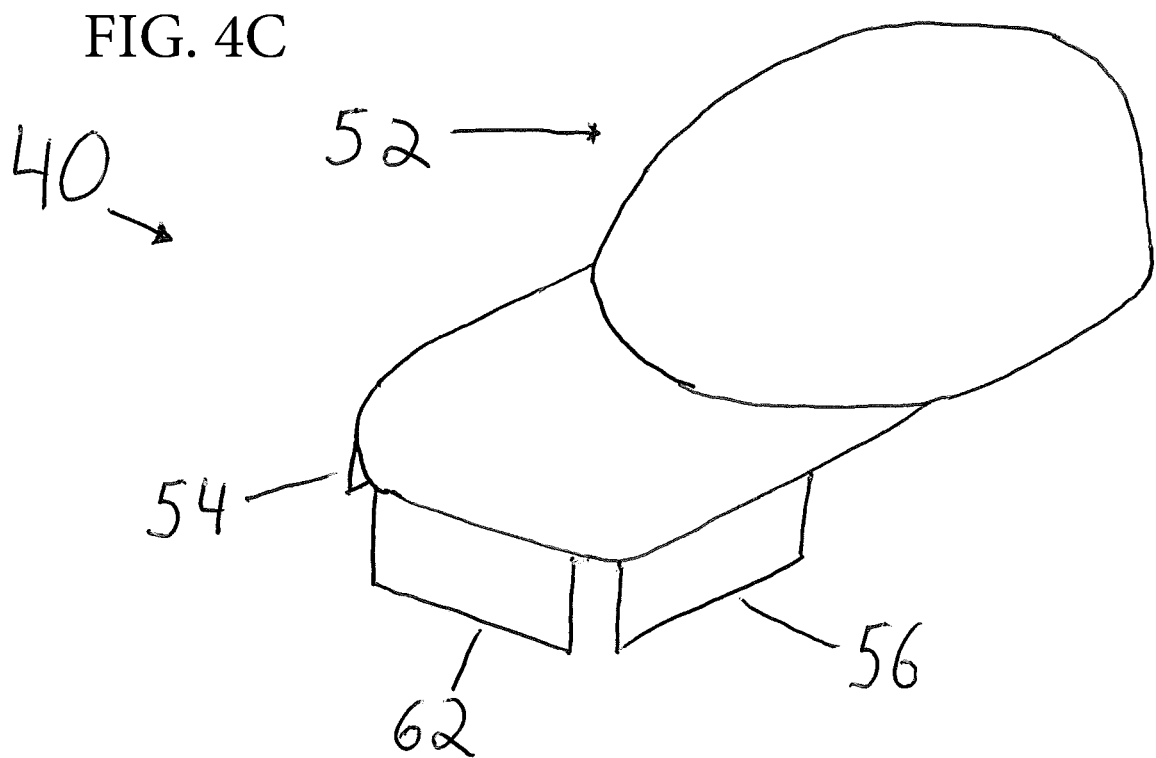
FIG. 4C is a front perspective view of a headwear embodiment.
Figure 4D:
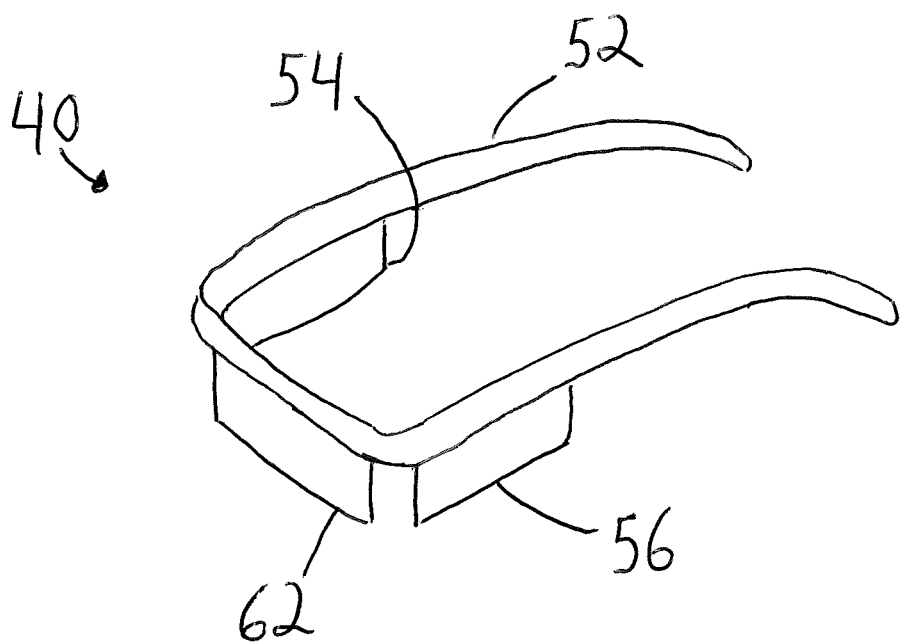
FIG. 4D is a front perspective view of an example of a headwear embodiment.
Figure 4E:
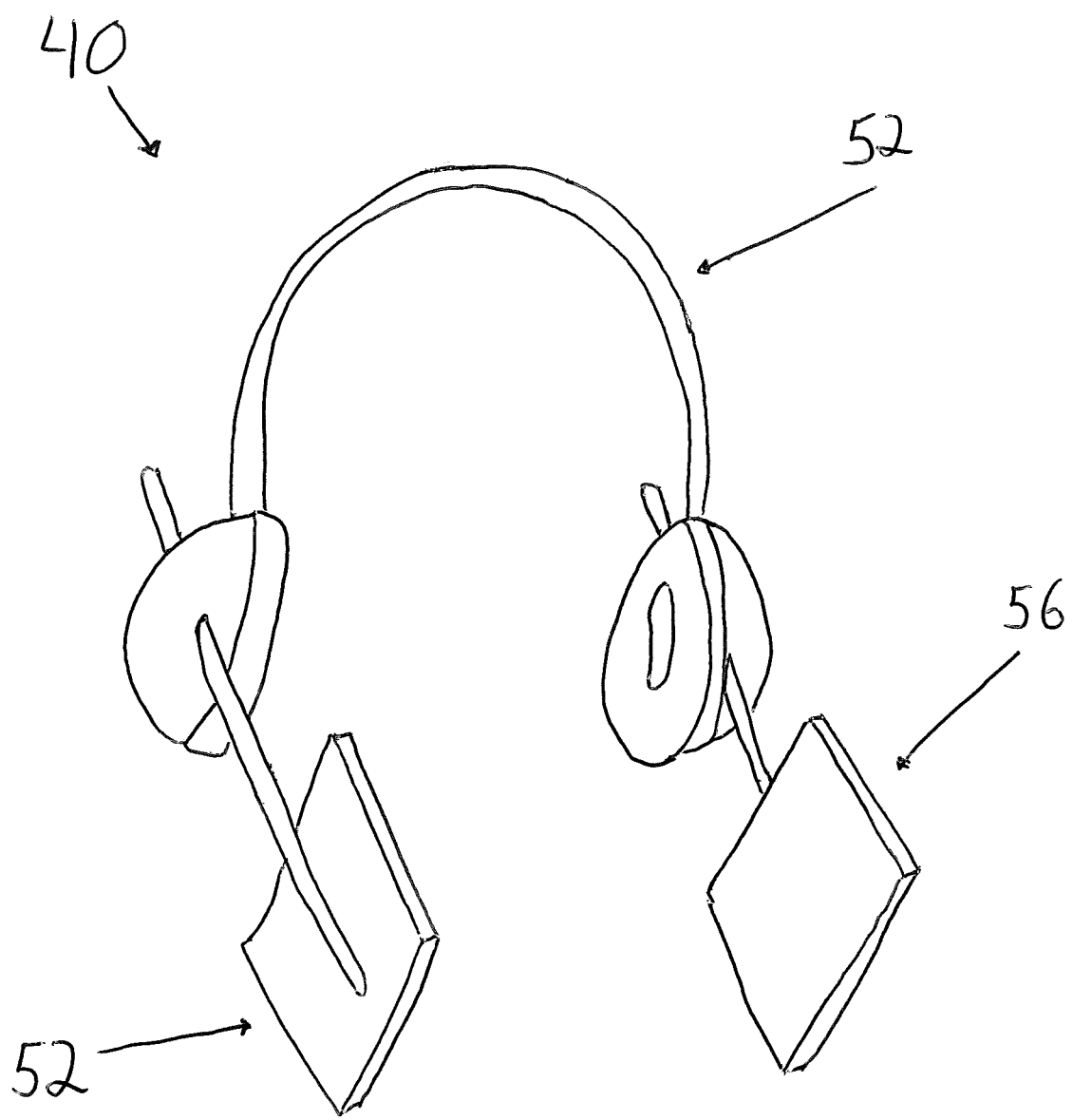
FIG. 4E is a front perspective view of an example of a headwear embodiment.

As shown in FIGS. 4A, 4B, 4C, 4D, and 4E, various types of headwear 40 are arranged to reduce a Cognitive Load in a user 12. Again, the user can be similar to the user for the system 10 and can have the field of vision 14, center vision 16, right eye peripheral vision 18, and left eye peripheral vision 20. The headwear 40 can include a structure or frame 52 shaped to be positioned on the head of the user 12. The frame 52 can be various frames and devices known to be placed on a head of a person, including, but not limited to, a hat, cap (FIG. 4A, 4B, 4C), eyewear (FIG. 4D), eyeglasses, sunglasses, and headphones (FIG. 4E). The frame 52 may come in a variety of sizes and shapes, but will be placed around the head and position display devices proximate to the field of vision 14 of the user 12.

The headwear 40 can further include the displays 54 and 56, similar in function to the display screens 24 and 26, which are sized to be attached to the frame 52. Further, the processor 28 and a computer readable memory 30 can also be operatively attached to the frame 52. Further, the headwear can include a third display 62, similar in function to the display screen 32, that is sized to be attached to the frame 52 and interact with the processor 28, computer readable memory 30, and displays 54 and 56. The displays 54 and 56 can be configured as previously described to block various portions of the right eye peripheral vision 18 and left eye peripheral vision 20.

In another embodiment the system 10 and/or headwear 40 can include noise adjusting or noise cancelling audio features. These audio features can include speaker or headphones that results in a dual-mode solution with both hearing and vision addressed. For example, as seen in FIG. 4E, earphones can be used on the frame 52 of the headwear 40. The earphones could be of the noise canceling type. The earphone speaker could also produce audio canceling sound, e.g. "white noise" to further reduce possible distractions to the user and lower the cognitive load on that use. Speaker as well as headphones could be used in the system 10 for the same purpose.

This largely completes discussion of FIGS. 1-10. FIGS. 11-17 will now be discussed.

In various of the embodiments of Cognitive Load Reduction systems shown herein, the systems are worn by a user. Doing so allows these various systems to be movable and less confining. As stated earlier, FIGS. 4A-4E show example non-limiting embodiments can include small displays attached to helmets, hats, caps, headphones, or apparatus on or over the head that fix the optical stimuli within a field of vision of the user. Some of the embodiments herein differ from other embodiments in that they achieve Cognitive Load Reduction in a more mobile, portable context, and with lighter weight and complexity. This in turn results in a user having the ability to employ various of the Cognitive Load Reduction systems described herein in a wider variety of environments than disclosed earlier.

Figure 11:
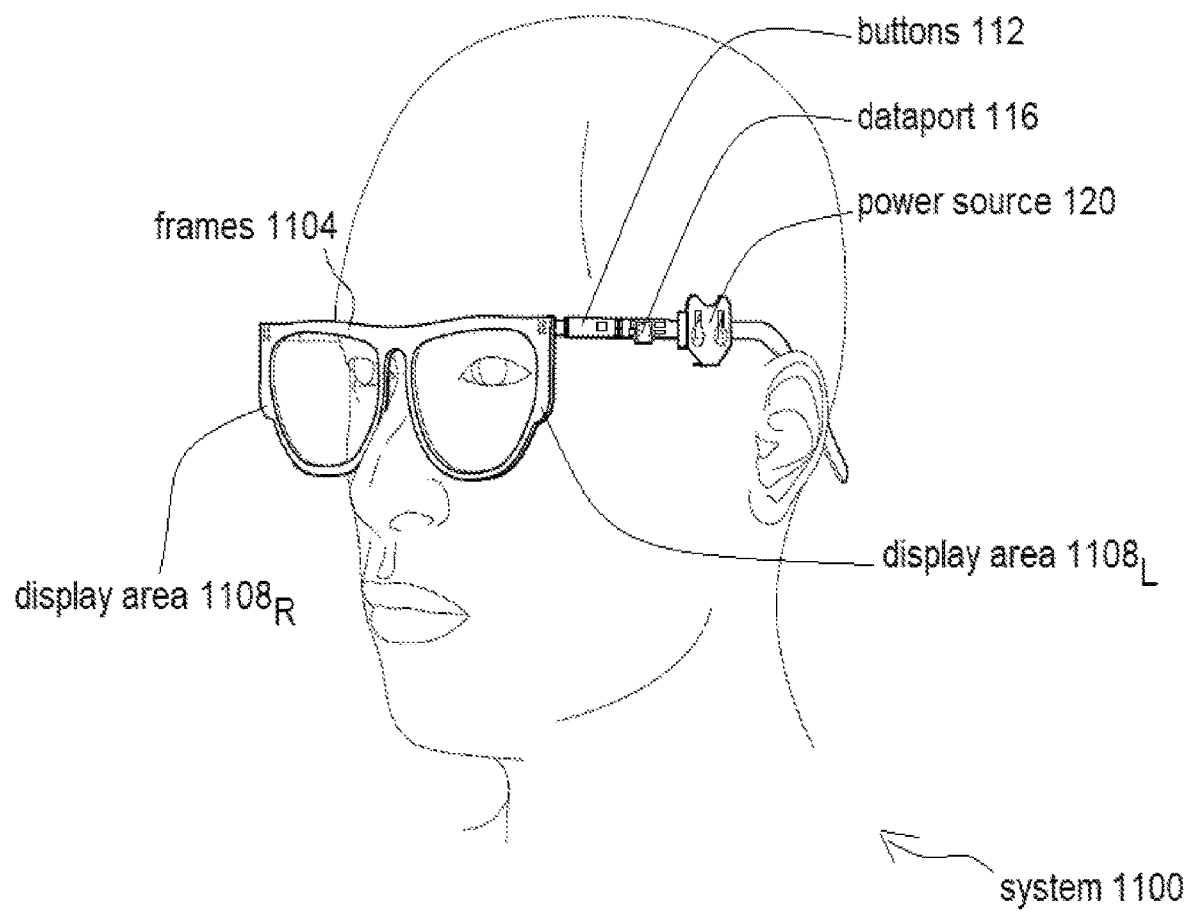
FIG. 11 shows an eyeglass system 100 for achieving Cognitive Load Reduction.

One example of this is shown in FIG. 11, which depicts an eyeglass system 1100 for achieving Cognitive Load Reduction. Specifically, the eyeglass system 1100 comprises a frame 1104, right and left display areas $1108_R$ and $1108_L$, a series of control buttons $1112_{1-n}$, a dataport connector 1116, and a rechargeable power source 1120.

Various other embodiments of Cognitive Load Reduction systems had a software component that would display different items on screens or a computer monitor, such as in FIG. 5. Meanwhile, for the eyeglasses embodiment (e.g. system 1100), a conventional computer monitor is not used. Instead, various lighting, effects, and features are built into the eyeglass frame 1104 itself, specifically the display areas 11088 and $1108_L$. in the form of lighting 1504 (not clearly visible in FIG. 11).

A portion of code drives the various control buttons $1112_{1-n}$ (for e.g. changing color, speed, duration, intensity, direction, diffusion), which are typically located on the frame 104. However, one focus of this disclosure is the pattern/movement of the lighting 1504 within the display areas $1108_{R\setminus L}$. The lighting 1504 is not clearly visible in FIG. 11 (obscured from view), and instead will be discussed in more detail with respect to FIGS. 15A-C.

The frame 1104 of the eyeglass system 1100 could be manufactured using a clamshell method, e.g. injection molded, although other methods may also be used. Some embodiments may be 3D printed, experimented with, and then the most effective designs have their STL files converted into injection molds, for larger-scale manufacture.

The frame 1104 is manufactured with apertures, grooves, and snap-in connections for attaching and removing the display areas 1108. Because the display areas 1108 will have some complexity and advanced lighting features, it will be helpful that the display areas 1108 to have their own testing and debug capability. The manufacturing environment for producing the embodiments herein will have a test bench for debugging and improving the various components discussed herein, and that test bench will include mechanisms for isolating just the display areas 1108.

Figure 12:
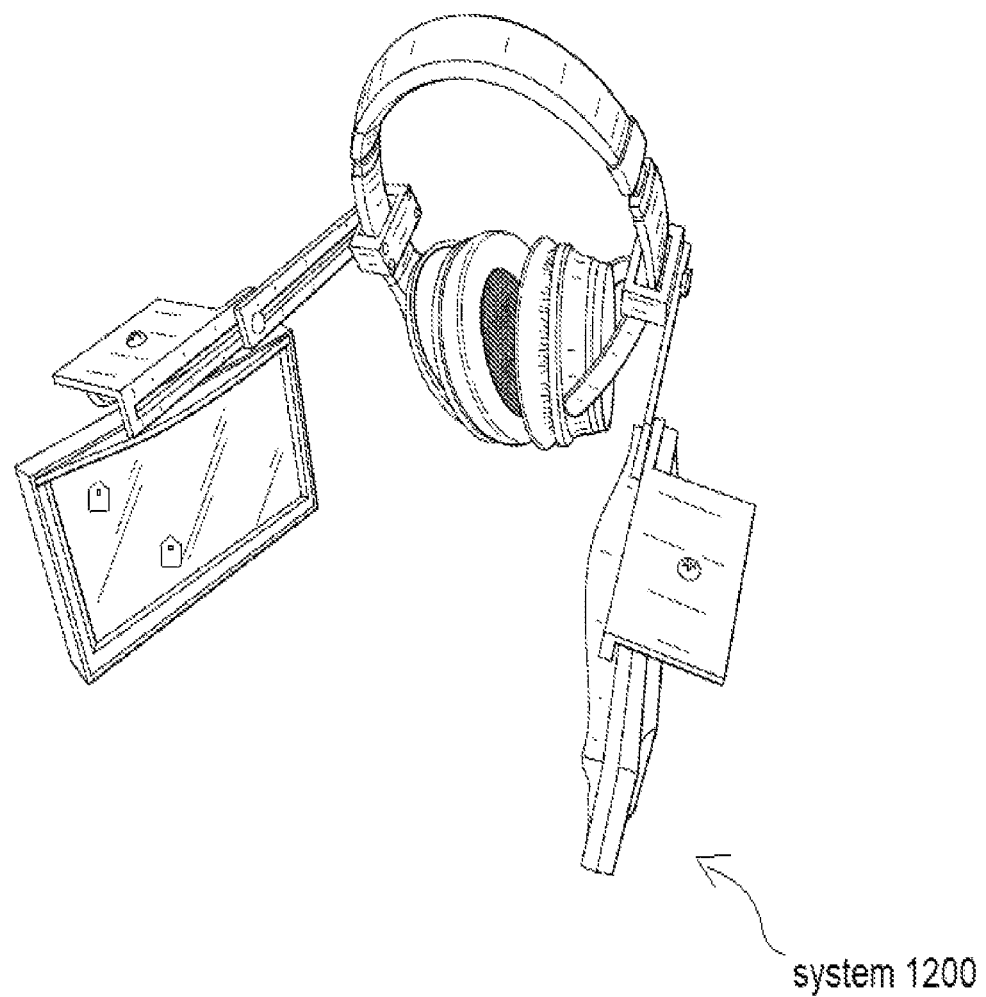
FIG. 12 shows a headphone embodiment of a Cognitive Load Reduction system.
Figure 13:
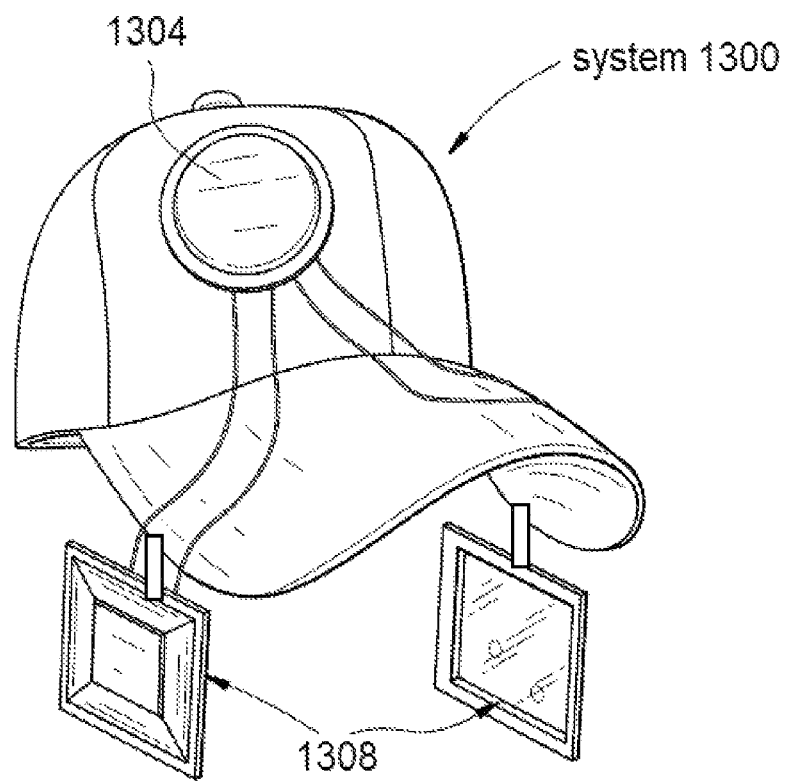
FIG. 13 shows an example Cognitive Load Reduction system using hats.
Figure 14:
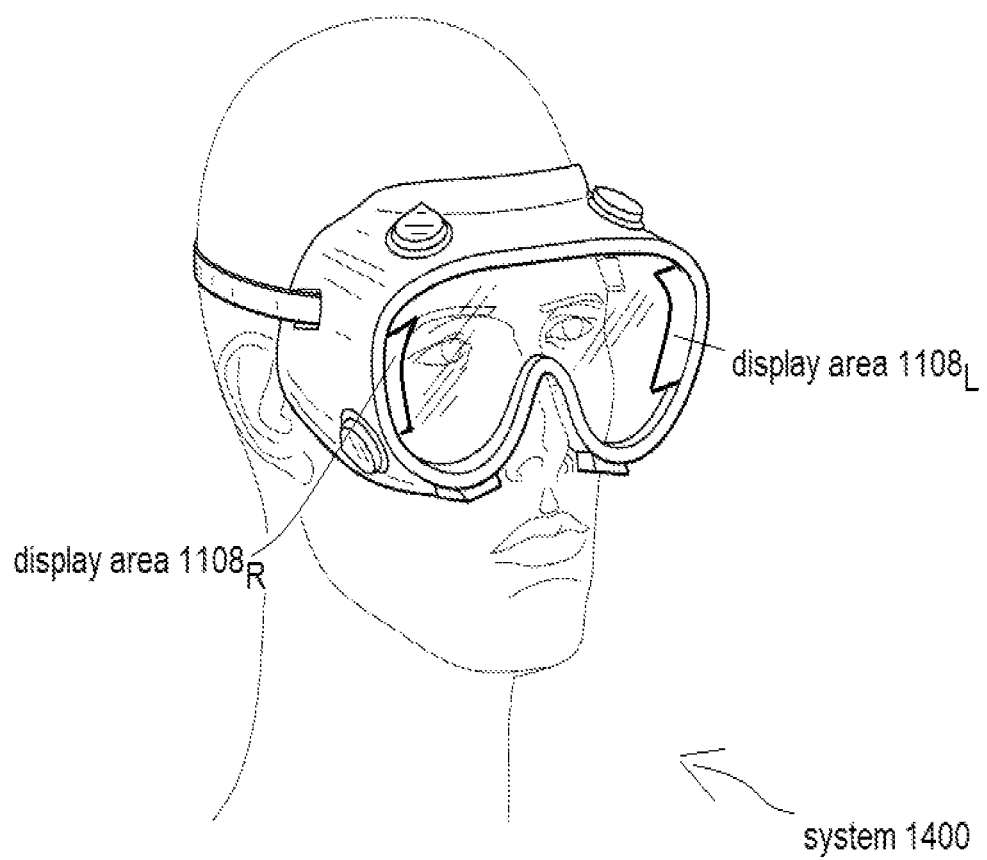
FIG. 14 shows an example safety goggle system.

FIG. 12 shows a headphone embodiment of a Cognitive Load Reduction system 1200. FIG. 13 shows an example Cognitive Load Reduction system 1300 using e.g. hats, helmets, or caps, and potentially other types of headgear. The system 1300 has electronics and battery pack 1304, and also side-mounted computer displays 1308. FIG. 14 shows a safety goggle system 1400 suitable for enhancing safety by reducing Cognitive Load and thereby enhancing user focus and retention. Prescription lenses can be included into the various eyeglass-goggle embodiments (e.g. systems 1100, 1400).

The embodiments herein can be used on any structure that can fix some type of optical generator within the field of view of the human eye. Wearing the various Cognitive Load reducing systems disclosed herein allows users to increase focus and learn faster and deeper while performing tasks on the move, standing, or in any environment where increased focus, learning ability, or fatigue reduction would be beneficial.

The post-testing, post-confirmation, consumer-ready, embodiments of the system 100 have additional components such as touch sensors that allow for that preset settings to be activated or changed based on a user's choice and preferences.

Figure 15A:
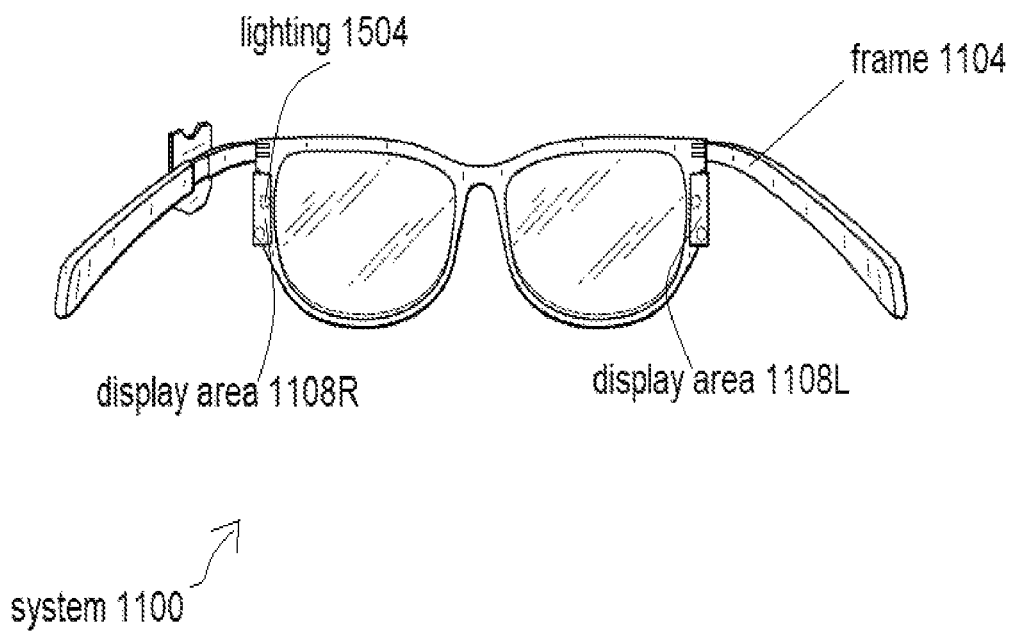
FIG. 15A shows more detail of the eyeglass system of FIG. 11.

FIG. 15A shows more detail of the eyeglass system 1100, specifically the lighting 1504. In an embodiment, the lighting 1504 is programmed to display a 'falling rain' pattern, adjustable based on data collected regarding highest consistently reproducible yield of Cognitive Load Reductions.

However, numerous additional embodiments are also disclosed herein, in which the downward movement is software-adjustable (user-adjustable) by any or all of intensity, diffusion, duration, size, color-balance, and potentially other factors. It is important to note that the expression "falling rain" is chosen for its descriptiveness. However, this specific movement should still be categorized as "non-biologic", noting how that specific expression is asserted within this disclosure by Applicant.

The specific color, and the type of lighting, within the lighting 1504 is chosen according to a variety of factors, although certain colors seem to be working well. For example, in some instances, green light is known to reduce migraines, and be soothing. In choosing the color/speed/duration of the lighting 1504 within the frames 1104/1550, one consideration is to achieve non-biological motion. Another consideration is to achieve randomization. In an embodiment, the lighting 1504 comprises LEDs.

Figure 15B:
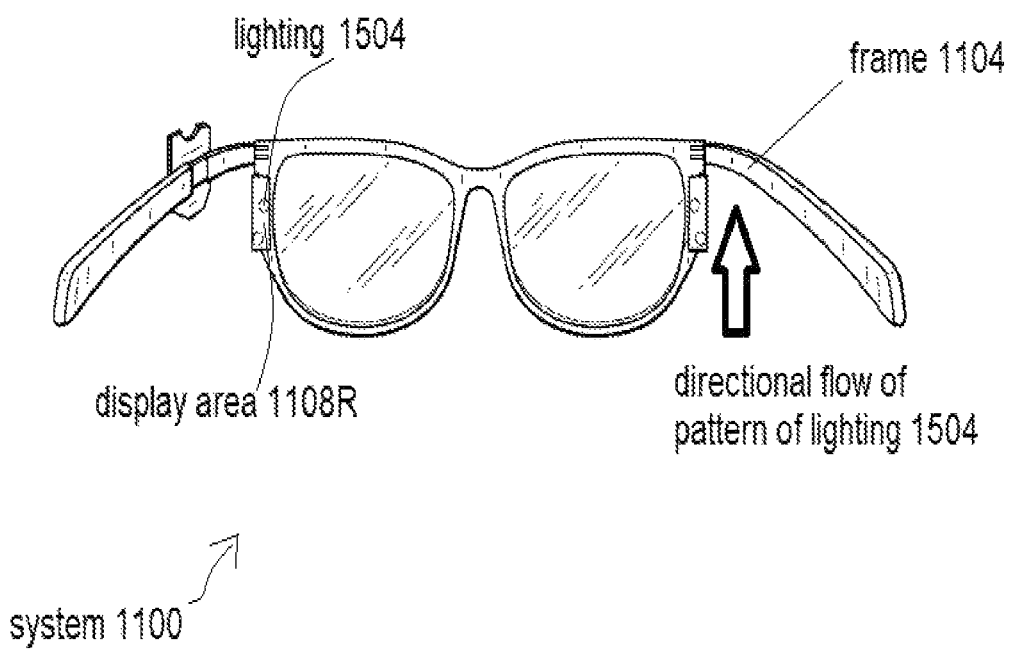
FIG. 15B shows an alternative embodiment where light-patterns move upwards.

In an embodiment, the raindrops (light-patterns) are not falling downwards within the lighting 1504 but instead are rising upward, as shown by the arrow of directional flow shown in FIG. 15B. This upward flow, not typically found in nature, would certainly fit within the concept of non-biologic movement. The light-patterns can also take an elliptical or curved route. Further, it is possible to vary the color, intensity, brightness, width, duration, diffusion of the lighting 1504. Even further, the light-patterns can comprise more than one light at the same time, with the light-patterns going in a semicircle, horizontal, faster/slower. Further, the light-patterns could comprise multiple rows/columns (with e.g. a middle column or row left disabled). In a further embodiment, the light patterns have differing colors in use at the same time, where for example, a green pattern can be traveling faster, and an orange pattern can be traveling slower. Any pattern that can assist in achieve Cognitive Load Reduction will be considered.

Figure 15C:
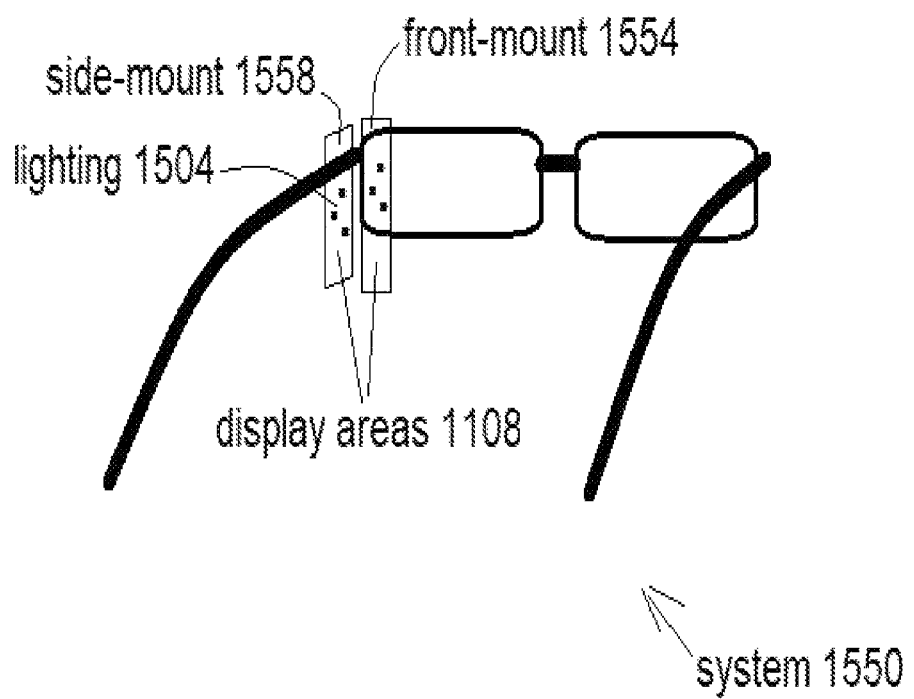
FIG. 15C shows drawings of an alternative frame embodiment.
Figure 16:
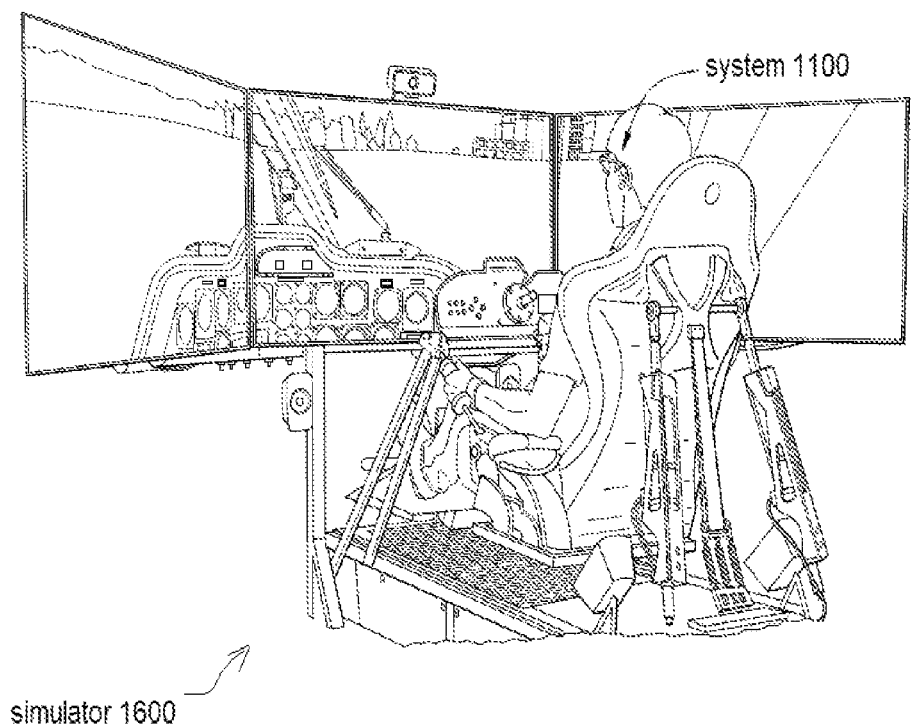
FIG. 16 shows a helicopter-training simulator.

FIG. 15C shows drawings of a wider glasses frame 1550 (not to scale) that in an embodiment can have a wider variety of lighting locations than what is shown in FIG. 15A. Further, the frame 1550 can have display areas 1108 set up as front sections 1554 and/or side sections 1558. For convenience, FIG. 15C is set up to only show the front section 1554 and side section 1558 on one side of the frame, but that is for convenience and clarity only, and thus should not be considered limiting.

FIG. 15C shows the same lighting 1504 as in FIG. 11, but this is for illustration-only and should not be considered limiting. The sections 1554/1558 may fasten to the wider frame 1550 in a different way than it fastened to the frames 1104, and may have more or less features.

The eyeglass system 1100 can also include features to make it easier to operate. This can include gnurled surfaces, raised bumps acting as a type of braille so that the user does not need to take off the frames 1104 in order to make changes in the lighting 1504.

Another potential usage of the embodiments herein is in training people faster, e.g. flight engineers. It costs a lot of money to train flight engineers. Thus, the various portable systems described herein provide an advantage in that they promote learning better and deeper, better retention. Further, their portability means they can be employed in highly specialize and highly limited training environments, such as the helicopter-training simulator shown in FIG. 16. The system 1100 and others herein would be suitable for use in the simulator 1600 of FIG. 16. Meanwhile, the system shown in FIG. 5 would not work with the simulator 1600 of FIG. 16.

The embodiments herein, including the eyeglass system 1100 and other disclosed herein, could assist in some symptomatic aspect of a person's existing Cognitive Load profile, especially where that person may be impaired, by e.g. PTSD or injury. For example, people who have suffered concussions, e.g. NFL players, find their steady-state Cognitive Load consistently higher post-injury, as their brain is having to work harder to repair itself and also to process information. Unfortunately, this state may be not only during times of stress, but also in general, at-rest periods, hence the expression "steady state". This in turn makes distractions and external factors (e.g. part of their existing, steady-state Cognitive Load) harder to manage so that their brains either shut down or slow down due to what may be described as sensory bombardment issues. Sensory-wise, such persons are not able to take in as much information, given their neurological sensitivities. The result is that some information, including potentially information, just gets blocked out.

The embodiments herein are thus suitable for concussion-victims, reducing their Cognitive Load, achieving a type of quiet-the-brain effect, which in turn allows the brain to heal faster. Further, the portable versions of the embodiments herein, e.g. the systems 1100\1200\1300\1400, have an advantage that they can be put into place immediately after a concussion takes place.

Testing and Data-Gathering, Achieving Effective Proof-of-Concept

A key to the success of the embodiments herein is believability and credibility. This field (assessing cognitive load and concentration-enhancement, achieving reduction in cognitive load) is rife with quack products, cons, and scams. Thus, overcoming initial skepticism and showing credibility is critical to the success of the embodiments herein.

Accordingly, an important principle of the embodiments herein it that the testing, verification of effectiveness, and solid proof-of-concept is performed by persons who have no vested interest in the outcome, or are given only minimal information as to the purpose of the invention, in order that they do not subconsciously skew their results to be more favorable to the manufacturers.

As stated, the individuals taking the various tests are tested against only themselves. That is, a group of tests without the embodiments herein are administered. Then, a similar group of tests using the embodiments herein are administered. Improvement in Cognitive Load Reduction will of course vary depending on a particular user, and vary according to a group of users' susceptibilities to different types of visual stimuli. But the resulting aggregate improvements will be unmistakable, and not dismissible due to statistical aberration. Because all other variations in environment are controlled and removed, the only remaining explanation for the improved test results, the improved concentration, the Cognitive Load Reduction, must be due to the embodiments herein. Everything else is exactly the same.

One early embodiment uses a mouse clicking exercise as a test/verification exercise. This exercise compares the overall effectiveness of the user after they're done based on multiple criteria. Testing will include but is not limited to accuracy, speed, and other variables that have a direct correlation with a scoring system showing overall effectiveness of concentration. In one embodiment, a group of ~50 subjects took various of the tests described herein, and found "statistically significant improvement" in concentration. The test used was the mouse target clicking exercise, but numerous other testing styles and modes are also used, as is discussed in more detail elsewhere herein.

As stated, an example test can comprise mouse-accuracy exercises (clicking on temporary dots as they briefly appear). Another is reading comprehension exercises (multi-choice, e.g. choices 'a' thru 'e'), including varying the speed and duration. An important factor of the embodiments herein is to increase accuracy of testing and decrease random correct answers based solely on guessing. Multi-choice tests having 5 choices are more difficult and require more concentration than 4 choices, and also reduce the chance of a false positive.

Another suitable test for Cognitive Load can be keeping a mouse-path properly stabilized while traversing within a maze. The amount of sheer calculating brainpower required by this test is not high, but the amount of eye-hand coordination and thus concentration is still high. A medium-strength concentration task might be doing exercises in addition and subtraction. At the far end of the concentration spectrum, a suitable high-concentration task might be a game of blackjack, counting cards in a 6-deck shoe. This task is known to require extremely high amount of concentration and ability to block out everything else. Thus, such a task is especially subject to noticeable gains from the embodiments herein, where these gains can be affirmed and verified by the right kind of testing.

Regardless of which kind of test is used, the embodiments of testing/verification of the effectiveness of the Cognitive Load Reduction discussed herein strive to use objective, reproducible metrics that can be independently verified. A specific criteria-set employed with the embodiments herein is Reproducibility, Accuracy, Effectiveness, and Validity (RAEV).

Thus, in an embodiment, bland generic testing mechanisms such as mouse-accuracy are used, as these are likely to be interpreted the same by any given person, regardless of that person's technical proficiency, age, gender, emotional stability, or interest in mouse-oriented activities such as gaming. Same with arithmetic tests, again because the person is merely being compared against themselves. Thus, math ability is immaterial to the testing discussed herein. Such a testing framework also eliminates any kind of bias due to gender, age, mental outlook, or previous computer-mouse experience (or lack thereof). This is because the same person takes the same type of test on that same day and preferably within the same hour. As a result, the testing environment is controlled to remove all extraneous variables.

Accordingly, within this disclosure, mouse clicking software is one possible testing example, mainly because it provides a convenient and easily measurable example of an environment in which a person's concentration-level has a direct correlation to the test-results. If a test-taker's concentration is impaired, or impacted, this will be found out by the mouse clicking software. The possibility of a wild guess is completely eliminated.

However, in a broader sense, all of the various tests shown herein are chosen, refined, and curated such that no person, no matter how proficient, can "fake" their way through the tests. The mouse-accuracy software test is just one example. The arithmetic tests are another, especially under timed circumstances. Further, even considering the case where some type of savant math-genius along the lines of Good Will Hunting answers all the questions perfectly, harder tests can be found, and run at a higher speed. Further, remember that the test-taker is not competing with other test takers, but instead is competing only with himself. Thus, the testing embodiments herein screen, filter, and are not harmed by people with unusual abilities. Various of the embodiments herein were tested using population-groups larger than 50 persons. This gives a richer and more in-depth pool of data, which is less likely to be subject to some type of statistical aberrations, outliers, or Will Hunting.

Next, a wide variety of differing types and styles of tests can be used. First to verify that the invention achieves tangible gains in managing cognitive loads. Second to also verify which types of high-concentration learning activities are most positively impacted by the embodiments herein, and in which configurations (e.g. the specific colors used within the light-patterns). This information is useful in steering and positioning the embodiments herein to the proper end-users and target audiences. This is valuable because not all high-concentration learning tasks will be affected the same way by the embodiments herein. Some learning tasks will achieve higher gains than others.

The tests should have some amount of tedium and drudgery, not be too enjoyable such that endorphin-flow manufactures extra levels of concentration. Along these lines, one good example is the card-game "concentration", first with a 52-card deck and then potentially a two-deck shoe. Meanwhile, video games e.g. "Call of Duty"® are not optimal, because even though these games are demanding, some people enjoy these games so much that they could block out anything, even a hurricane, and not be impaired. As such, some level of tediousness in the tests is actually helpful for proving out the embodiments herein.

Testing Environment

In a medical internship, an aspiring medical doctor may be required to stay awake for as long as 24 hours at a stretch. Part of this is intentional, that a typical medical doctor is tasked with a lot of medical decisions at any given time, but often these medical decisions must be addressed immediately and cannot be postponed until a more convenient time. Thus, a medical doctor must show capability of good concentration and good decision-making even at times where they may be impaired, that is, where they are carrying a very heavy Cognitive Load, either due to fatigue, stress, sleep-deprivation, or other factors.

As such, regarding the embodiments herein, the best test-results may be when a person already has some extra Cognitive Load. One way to emulate this is to position people at both side of the test-taker, such that the test-taker is in a "middle-seat-on-an-airplane" environment, an annoyance which definitely adds to a Cognitive Load. Another is to have the room temperature unusually low, but where the user is wearing only a T-shirt, so that the user is cold. This also adds to a person's Cognitive Load. As stated, as long as the middle-seat persons must be situated exactly the same for both tests (that is, the without/with).

Most important, as stated, the tests are always performed in pairs, that is, one "control" test administered without any of the embodiments herein. Then, as soon as possible afterwards, performing the exact same type\category of test (using the example of arithmetic, the second test would have the same test-format, just with different numbers). As stated, within the embodiments herein, the test-environment is controlled such that the only variable is the Cognitive Load Reduction systems discussed herein. Any barking dogs, runny noses, middle seat, all those factors, must be the same during both tests (both without/with the embodiments herein, typically in that order), in order to get an idea of how much the user was affected by the embodiments herein.

Another important testing factor is that the participants must leave their mobile devices outside the testing area, and not be influenced in any way by outside considerations. Mobile devices are known to be powerfully hypnotic, addictive, and absolutely ruin any attempt to test for CLR. However, the specific computing devices used within the testing might be stationary/desktop, or might be mobile, as both of these lead to excellent data tracking. However, all computing devices will be operated in Internet-disabled mode, where the only the thing the user can do on the device is take the tests.

Next, it is understood that most people in real-life situations do not function like this, where they are single-focused on only one task. However, the testing embodiments disclosed herein are not meant to fully and completely emulate real-life situations. Instead, the testing embodiments are meant to exactly quantify a difference between Cognitive Load without the systems disclosed herein, and then with, and compare the difference.

Next, many physical embodiments of the testing systems exist. In the embodiment of helicopter emulation (FIG. 16), any embodiment using side-blinders (e.g. the systems 200\300 shown in FIGS. 12 and 13) will potentially be avoided. As such, in evaluating Cognitive Load Reduction in the helicopter-emulation environment, it is preferred to focus more on the eye glass/goggle embodiments, as peripheral vision must not be blocked. This is because peripheral vision is an important part of flight/helicopter training. Thus, the embodiments herein most suitable for this training should not impede peripheral vision whatsoever.

Another key principle of the embodiments herein is to extrapolate from individual results to group\aggregate results. One example could be that, in general, over a wide variety of test-subjects, where the users vary in age, ability to concentrate, physical health, or other factors, certain colors may work better than other. That is, certain colors may achieve Cognitive Load Reduction better than other colors.

FIGS. 17A and 17B show a high-level approximation of this extrapolation from individual to group\aggregate. FIG. 17A shows a summary of a testing methodology 1704 for individuals, while FIG. 17B shows a summary of a testing methodology 1708 for groups. Both methodologies strive to improve reproducibility, accuracy, effectiveness, and validity (RAEV) of both the testing, and also of the various embodiments and combinations being tested.

Another key principle of the embodiments herein is to survey the test-takers and try to get user-feedback. A user may note that their Cognitive Load Reduction occurred using a certain color, but that same color also caused them more headaches or eyestrain. The embodiments herein take these surveys only at the end, where Applicant then curates the most germane and relevant remarks and applies them to later tests.

The testing environments discussed herein also require stabilizing caffeine levels. It is well-known that caffeine can change a person's concentration-levels, even from one 10-minute segment to another. The testing embodiments herein control for that.

Overall Testing Principle

In refining the embodiments herein, there are two main principles in use, one obvious and the other not. The first principle is that the experimenting and testing discussed herein strives to improve the invention itself, the CLR system. However, a second less obvious principle is the iterative improvement of just the testing itself. Determining which tests to keep, which to toss out, which tests to refine, is also important to the embodiments herein. This information is invaluable in determining which features of the embodiments herein to include, which to enhance, which to omit. e.g. which colors to keep, which colors to throw out, which colors to refine. Same with many other features, such as the exact location of the lighting 1504 within the eyeglass\goggle embodiments, how many lights 1504 to include, how to sequence their operation, what is overload v. what is effective, and many other product-enhancement principles. Better testing leads to a better product.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations, or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations, or equivalents. It is intended that the following claims define the scope of the invention and that methods and structures within the scope of these claims and their equivalents be covered thereby.

What is claimed is:

1. A method for manufacturing a system for reducing cognitive load, comprising:
   manufacturing a wearable product to have a frame comprising a plurality of apertures for permanently inserting one or more display areas;
   configuring the frame to have one or more apertures, grooves, and snap-in connections suitable for accepting user-selection mechanisms;
   manufacturing the one or more display areas;
   manufacturing the user-selection mechanisms;
   locating one or more lighting mechanisms within the one or more display areas;
   connecting the user-selection mechanisms to the frame;
   connecting the display areas to the frame;
   the user-selection mechanisms comprising buttons;
   the buttons comprising raised and engraved patterns for assisting a user in making choices and selections in a configuration of the lighting where that use can do so without removing the frame.

2. The method of claim 1, further comprising:
   the lighting mechanisms comprising LEDs.

3. The method of claim 1, further comprising:
   the display areas comprising right and left display areas.

4. The method of claim 1, further comprising:
   configuring the buttons to be responsive to a portion of code connected to the lighting mechanisms and facilitating a user changing any of color, speed, duration, intensity, direction, diffusion of and lighted patterns.

5. The method of claim 1, further comprising:
   manufacturing the frame using clamshell injection molding.

6. The method of claim 1, further comprising:
   manufacturing the one or more display areas to have their own testing and debug ports, separate from the frame.

7. The method of claim 6, further comprising:
   arranging a manufacturing environment used in producing the frame and lighting to have a test bench for debugging and improving the various components discussed herein; and
   the test bench incorporating mechanisms for connecting to the ports within the display areas.

8. The method of claim 1, further comprising:
   manufacturing the frame in the form of headphones.

9. The method of claim 1, further comprising:
   manufacturing the frame in the form of goggles.

10. The method of claim 9, further comprising:
    incorporating prescription lenses directly into the goggles.

11. The method of claim 1, further comprising:
    arranging the lighting to display a falling rain pattern.

12. The method of claim 1, further comprising:
    arranging the lighting to display a non-biologic pattern.

13. The method of claim 12, further comprising:
    arranging for the light patterns to be rising upward.

14. The method of claim 13, further comprising:
    arranging for the light-patterns to comprise two or more lighting sequences at the same time.

15. The method of claim 1, further comprising:
    manufacturing the one or more display areas to comprise both front and side sections, where the front section is located on a frame portion in front of a user's eye, and the side section is located on a frame portion to a side a user's eye.

16. The method of claim 1, further comprising:
manufacturing the one or more lighting patterns to comprise multiple rows/columns.

17. The method of claim 16, further comprising:
the light patterns have differing colors in use at the same time.

18. The method of claim 1, further comprising:
utilizing the system within a helicopter-training simulator.

\* \* \* \* \*